United States Patent [19]
Berndt

[11] Patent Number: 5,817,507
[45] Date of Patent: Oct. 6, 1998

[54] BLOOD CULTURE APPARATUS HAVING A BELL-SHAPED DRUM

[75] Inventor: Klaus W. Berndt, Stewartstown, Pa.

[73] Assignee: Becton Dickinson and Company, Franklin Lakes, N.J.

[21] Appl. No.: 721,879

[22] Filed: Sep. 27, 1996

[51] Int. Cl.⁶ .................................................... C12M 1/34
[52] U.S. Cl. .................................. 435/287.3; 435/288.1; 435/288.7; 435/303.3; 356/428; 422/64
[58] Field of Search .............................. 435/286.2, 289.3, 435/287.9, 288.1, 288.7, 303.1, 303.3, 304.1, 808, 809; 422/63–66, 82.05, 82.11; 250/576, 328; 356/426–428

[56] References Cited

U.S. PATENT DOCUMENTS

| | | | |
|---|---|---|---|
| 4,940,332 | 7/1990 | Miwa et al. | 435/288.7 |
| 5,498,543 | 3/1996 | Berndt | 435/287.3 |
| 5,516,692 | 5/1996 | Berndt | 435/288.7 |
| 5,518,923 | 5/1996 | Berndt | 435/288.7 |

*Primary Examiner*—William H. Beisner
*Attorney, Agent, or Firm*—Alan W. Fiedler

[57] ABSTRACT

The present invention describes an automated blood culture apparatus having a bell-shaped hollow rotatable drum for holding a number of blood culture bottles. All bottles are interrogated by sensor stations located within the drum with the whole system having only one moving part, and no flexible electric or optic cables. Consequently, the expected reliability is high, and the production cost should be low. The apparatus also includes an "auto-unloading" and sorting mechanism for sorting final "negative" and "positive" bottles.

8 Claims, 6 Drawing Sheets

BLOOD CULTURE APPARATUS HAVING A BELL-SHAPED DRUM

BACKGROUND OF THE INVENTION

1. Field of the Invention

The present invention relates to a non-invasive apparatus for detecting biological activities in a specimen such as blood, where a number of specimens with culture medium are introduced into a large number of sealable containers and are exposed to conditions enabling a variety of metabolic, physical, and chemical changes to take place in the presence of microorganisms in the sample. These changes are then monitored using calorimetric or fluorescent chemical sensors disposed to the inner bottom of each blood culture bottle as the bottles are rotated in a bell-shaped rotatable drum. After monitoring is complete, the apparatus performs "auto-unloading" and sorting of final negative and final positive bottles.

2. Background Description

The presence of biologically active agents such as bacteria in a patient's body fluid, especially blood, is generally determined using blood culture bottles. A small quantity of blood is injected through an enclosing rubber septum into a sterile bottle containing a culture medium, and the bottle is then incubated at 37° C. and monitored for microorganism growth.

One of the techniques used to detect the presence of microorganisms includes visual inspection. Generally, visual inspection involves monitoring the turbidity or eventual color changes of the liquid suspension of blood and culture medium. Known instrumental methods detect changes in the carbon dioxide content of the culture bottles, which is a metabolic by-product of the bacterial growth. Monitoring the carbon dioxide content can be accomplished by methods well established in the art, such as radiochemical or infrared absorption at a carbon dioxide spectral line. Until now, these methods have required invasive procedures which result in the well-known problem of cross-contamination between different bottles. It has also been proposed to detect microorganism growth in sealable containers by monitoring positive and/or negative pressure changes.

Recently, non-invasive methods have been developed involving chemical sensors disposed inside the bottle. These sensors respond to changes in the pH, carbon dioxide or oxygen concentration by changing their color or by changing their fluorescence intensity. In known automated non-invasive blood culture systems, individual light sources, spectral excitation/emission filters, and photodetectors are arranged adjacent to each bottle. This results in station sensitivity variations from one bottle to the next. Additional problems are caused by the aging effects of the light sources, filters and photodetectors. Due to the fact that most known blood culture sensors generate only a moderate contrast ratio in the measured photocurrent during bacterial growth, extensive and time-consuming calibration procedures and sophisticated detection algorithms are required to operate these systems. In addition, because of required bottle agitation flexible electrical cables are required to connect the individual sources and detectors with the rest of the instrument. With the large number of light sources, typically 240 or more per instrument, maintenance can become very cumbersome and expensive when individual sources start to fail.

In all known colorimetric or fluorometric instruments, light emitting diodes (LEDs) are used as the individual light sources. These sources have only a relatively low optical output power. Therefore, a high photometric detection sensitivity is required to monitor the bottle sensor emissions. In the case of fluorescent sensors, this means an extra effort with regard to the front-end electronics for each photodetector. As a result, production cost is relatively high.

It has been proposed already in U.S. Pat. No. 5,516,692, entitled "Compact Blood Culture Apparatus" to arrange a multitude of blood culture bottles on a rotating drum with sensor stations mounted to the instrument's mainframe at such a distance from the drum that, during rotation of the drum, individual bottles pass by these sensor stations. Each bottle has its inner bottom covered with a fluorescent chemical sensor and all the bottles in the rotating drum are contained in an incubator. Each bottle is inserted into the drum neck first such that the bottles are arranged radially on the rotating drum with their necks oriented towards the drum axis. With such an orientation, loading and un-loading of bottles is accomplished by grasping the bottles at their bottom and feeding them into the drum neck first. Due to the fact that bottles are commonly transported to the automated blood culture apparatus in an upright orientation, each bottle has to be grasped twice before loading. Since this requires additional work and microbiology lab personnel are accustomed to grasping bottles by their neck, there is a need to overcome the unusual situation of feeding blood culture bottles into the system with the neck first.

It has also been suggested in U.S. Pat. No. 5,498,543, entitled "Sub-Compact Blood Culture Apparatus" to split the drum into segments, wherein each segment forms a drawer that can be removed from the interior of the instrument when in the lowest position. In that way, the bottles are in an upright position and can be grasped by their neck during loading and unloading. A disadvantage of this solution is its mechanical complexity and the resulting manufacturing precision that is required. Consequently, there is still a need for a mechanically simple blood culture apparatus in which the bottles can be grasped by their necks during loading and unloading or, more importantly, an apparatus that can perform "auto-unloading" and sorting of final negative and final positive bottles.

SUMMARY OF THE INVENTION

The present invention overcomes the above problems by providing a blood culture apparatus for detecting biologically active agents in a large number of blood culture bottles, that is simple and can be produced at very low cost, provides low system sensitivity variations from one bottle station to the next, does not require electronic or optoelectronic components, electrical wires, or optical fibers on the moving bottle rack, has high long-time reliability, allows a user to grasp the bottles at their neck during loading and unloading, offers simultaneous access to a large number of bottles during loading and unloading, and has a smaller footprint as compared to existing blood culture systems.

According to the present invention, the above objectives are achieved by introducing a culture medium and the blood specimen into sealable glass bottles having optical sensing means on their inner bottom surface and by arranging a large number of such bottles radially on a rotating hollow bell-shaped drum within an incubator in such a way that their bottoms are oriented towards the drum axis. The bell-shaped drum is supported only on one end with sensor stations within the drum mounted to the instrument mainframe at such a distance inside the bell-shaped drum that, during rotation of the drum, individual bottles pass by these sensor stations.

In a preferred embodiment of the invention, the axis of the bell-shaped drum is oriented horizontally and parallel to a door on the front face of the incubator. Horizontal orientation of the axis provides maximum agitation of the liquid culture medium, blood specimen, and gas within each blood culture bottle. During the load/unload operation, the door is opened to allow simultaneous access to approximately one third of the bottles. Then, the drum is rotated until the next third of the bottles becomes accessible. Therefore, all bottles are accessible in three steps.

In another option of the current invention, the axis of the bell-shaped drum is oriented vertically with a slight tilting of approximately 20 degrees away from the door. By adjusting the tilting angle, the degree of agitation can be modified, if required.

Still another embodiment is a blood culture apparatus having an "auto-unloading" and sorting feature, wherein final negative and final positive bottles are ejected from the drum and sorted into a "negative" drawer or a "positive" drawer.

These and other aspects, features and advantages of the present invention will become apparent from the following detailed description, taken in conjunction with the accompanying drawings.

DETAILED DESCRIPTION

Figure 1:
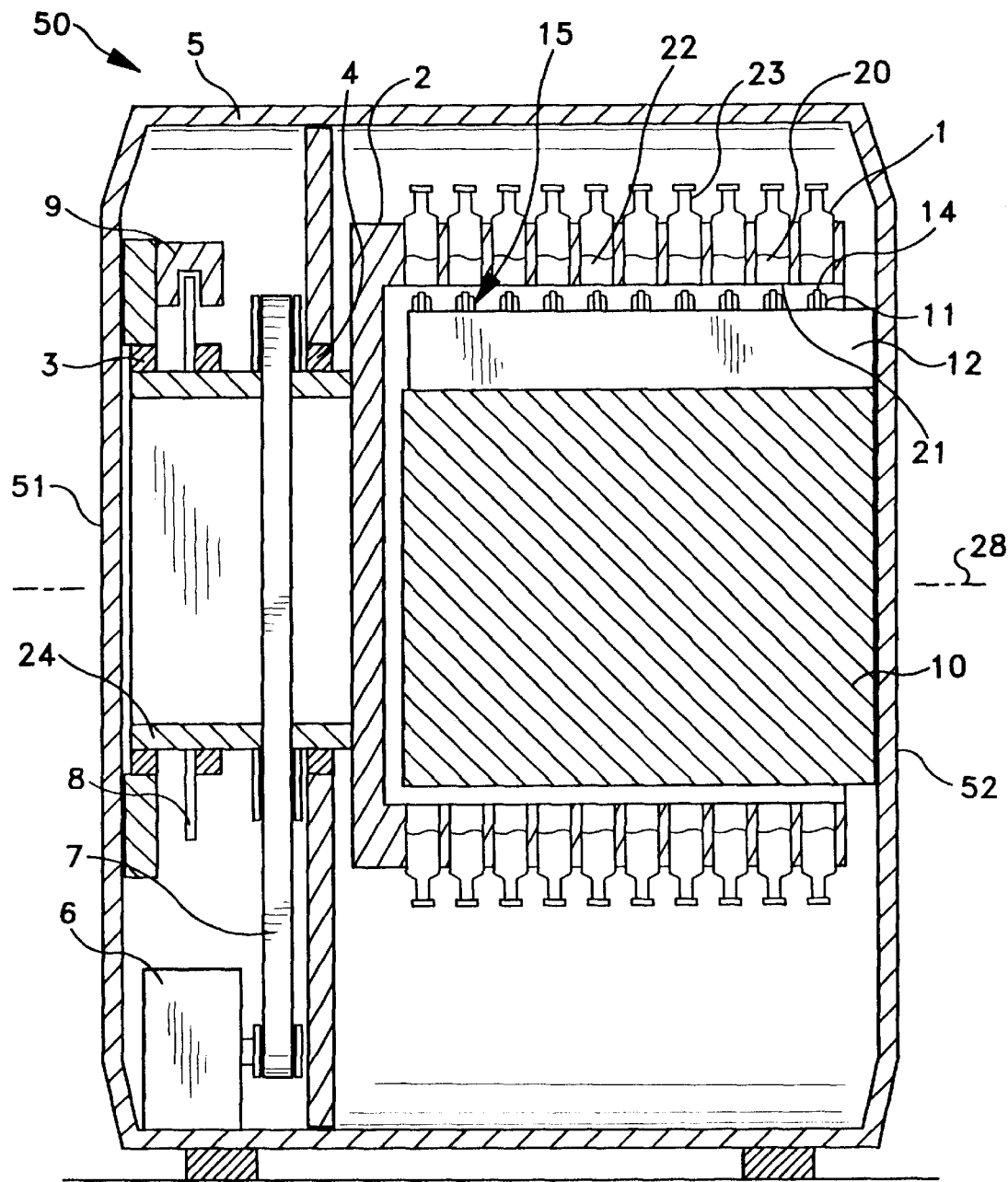
FIG. 1 shows a front-view of the interior of a blood culture apparatus for the detection of microorganisms according to the present invention.

According to the present invention, a culture medium and blood specimen mixture 22 are introduced into sealable glass bottles 1 that include optical chemical sensing means 20 on their inner bottom surface 21. Optical chemical sensing means 20 emanates differing quantities of light depending upon the amount of a gas in bottle 1. For example, the gas being detected by optical sensing means 20 can be carbon dioxide, oxygen or any gas that increases or decreases depending upon the presence or absence of microorganism growth in bottle 1.

Figure 2:
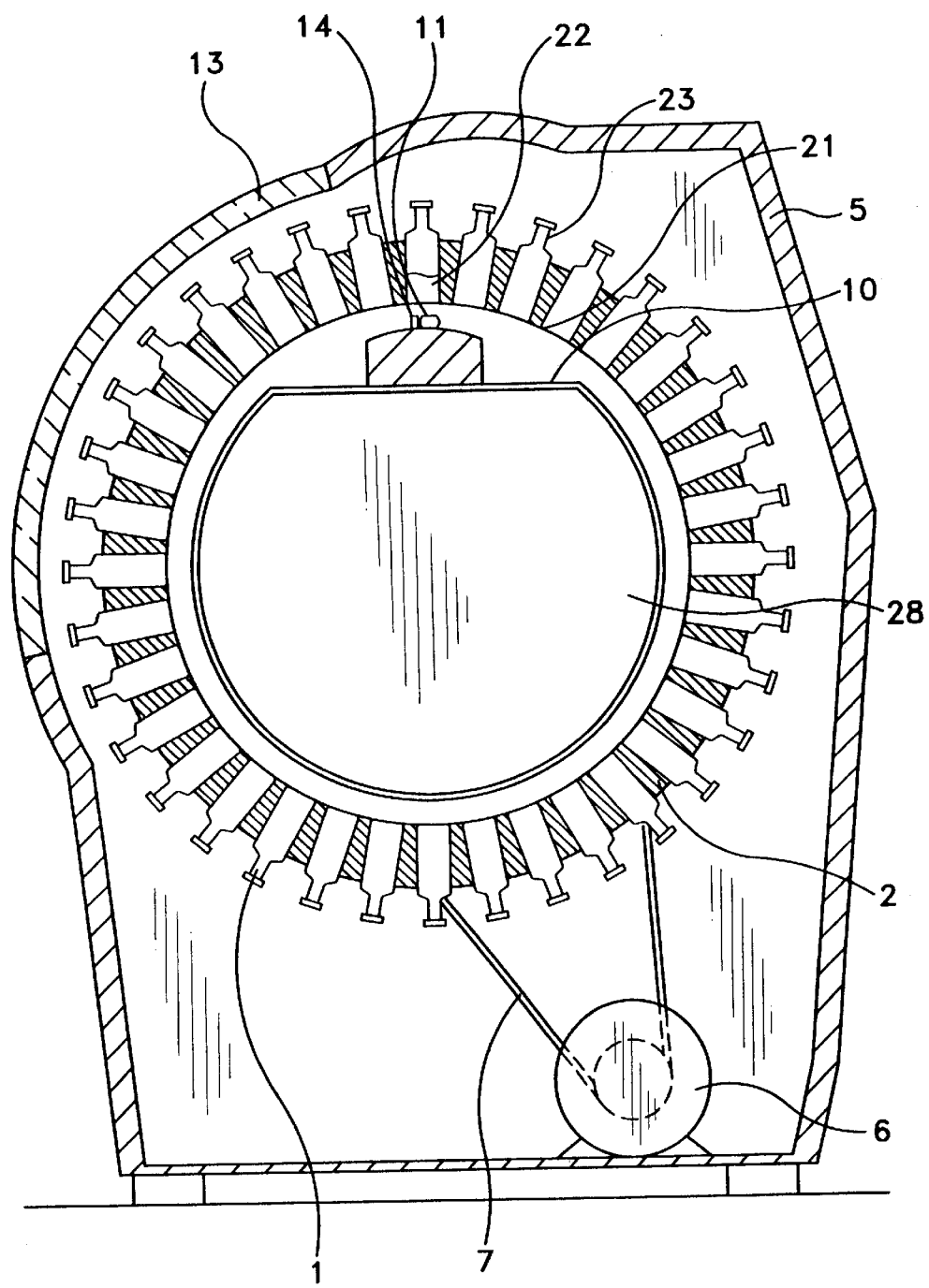
FIG. 2 shows a side-view of the interior of a blood culture apparatus according to the present invention.

As illustrated in FIGS. 1 and 2, a plurality of such bottles 1 are arranged radially on a rotating bell-shaped drum 2 within an incubator 5 in such a way that the bottoms of bottles 1 are oriented towards a drum axis 28. Bell-shaped drum 2 is hollow and is supported by a shaft 24 rotatably supported on one end by two large ball-bearings 3 and 4 mounted to a first side 51 of an instrument mainframe 50. In order to read information coming from each optical chemical sensing means 20 within bottles 1, a linear array of sensor stations 12 is mounted within rotating bell-shaped drum 2 to a second side 52 of instrument mainframe 50 at such a distance inside bell-shaped drum 2 that, during rotation of drum 2, individual bottles 1 are passing by respective sensor stations 15 in array 12. Each sensor station 15 of the linear array of sensor stations 12 comprises an excitation light source 11 and a collection end of an optical fiber 14.

In a preferred embodiment of the present invention, axis 28 of the bell-shaped drum 2 is oriented horizontally and parallel to a door 13, shown in FIG. 2, located on a front face of incubator 5. Horizontal orientation of axis 28 provides maximum agitation of the liquid culture medium and specimen mixture 22 and the gas within each bottle 1. During a load or unload operation, door 13 is opened which allows to access approximately one third of all bottles 1 simultaneously. Then, drum 2 is rotated until the next third of bottles 1 becomes accessible. In three steps, all bottles 1 are accessible.

Alternatively, axis 28 of bell-shaped drum 2 is oriented vertically with a slight tilting of approximately 20 degrees away from door 13. By adjusting the tilt angle, the degree of agitation can be modified, if required, for maintaining optimum growth conditions.

In operation, bell-shaped drum 2 is rotated by motor 6 and a belt 7. A circular member 8 and a sensor 9 form an angular encoder that provides information about which row of bottles 1 is passing sensor station array 12. Preferably, motor 6 is a stepper motor, allowing drum 2 to rotate either in a continuous mode or to stop drum 2 at appropriate angles to read from sensing means 20 within bottles 1 in a steady-state mode. The whole system is controlled by a control system 10 located inside rotating drum 2. Output ends of all optical fibers 14 of the linear array of sensor stations 12 are fed to one common photodetector (not shown) in control system 10 such that only one excitation light source 11 needs to be turned on at a time. Therefore, the control system "knows" from which sensing station 15 and, therefore, which bottle 1 the sensor light is being collected.

The apparatus shown in FIGS. 1 and 2 is merely exemplary and contains ten segments of blood culture bottles 1 with thirty six bottles 1 per segment. Consequently, the total capacity is 360 bottles. The arrangement of bottles 1 on drum 2 allows for a relatively high packaging density. Table 1 indicates the required size of the drum for different options comprising either 720, 360, 240, or 120 bottles. In Table 1, standard blood culture bottles as sold by Becton Dickinson Microbiology Systems, Sparks, Maryland, have been assumed, with the outer diameter D having been calculated with the bottles included. Table 1 also provides information as to the length L of the drum for different geometric options.

TABLE 1

| Number of Bottles | Bottles per Segment | Number of Segments | D (inch) | L (inch) |
|---|---|---|---|---|
| 720 | 36 | 20 | 34 | 40 |
| 360 | 36 | 10 | 34 | 20 |
| 360 | 18 | 20 | 23 | 40 |
| 240 | 24 | 10 | 27 | 20 |
| 240 | 12 | 20 | 19 | 40 |
| 120 | 24 | 5 | 27 | 10 |
| 120 | 15 | 8 | 21 | 16 |
| 120 | 12 | 10 | 19 | 20 |

For options with ten or more segments, it is possible to support the bell-shaped drum at the open end by two rollers mounted to the instrument's mainframe. In this way, any deformation of the drum can be avoided.

Figure 3:
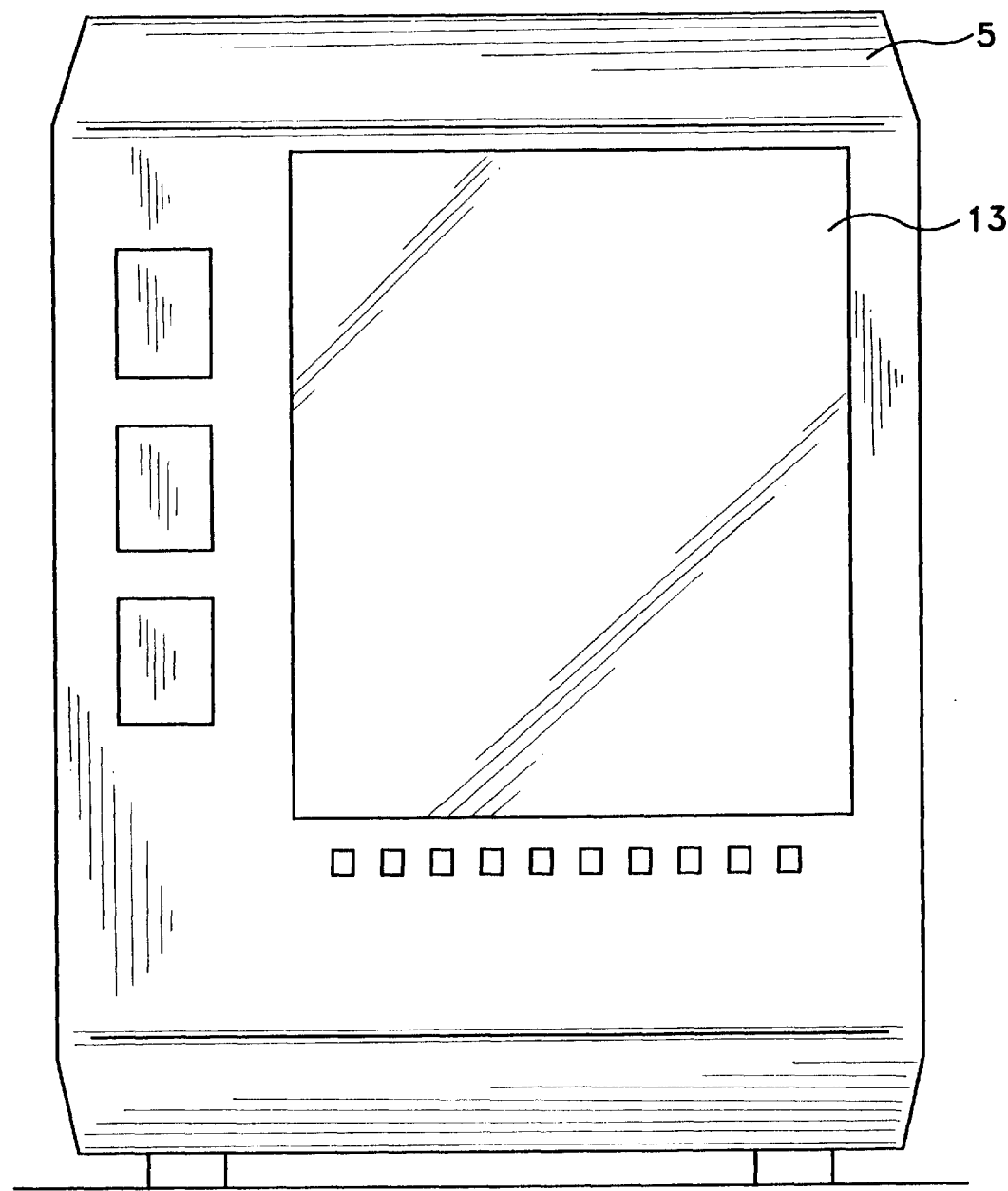
FIG. 3 shows a front-view of a blood culture apparatus according to the present invention, with the door closed.
Figure 4:
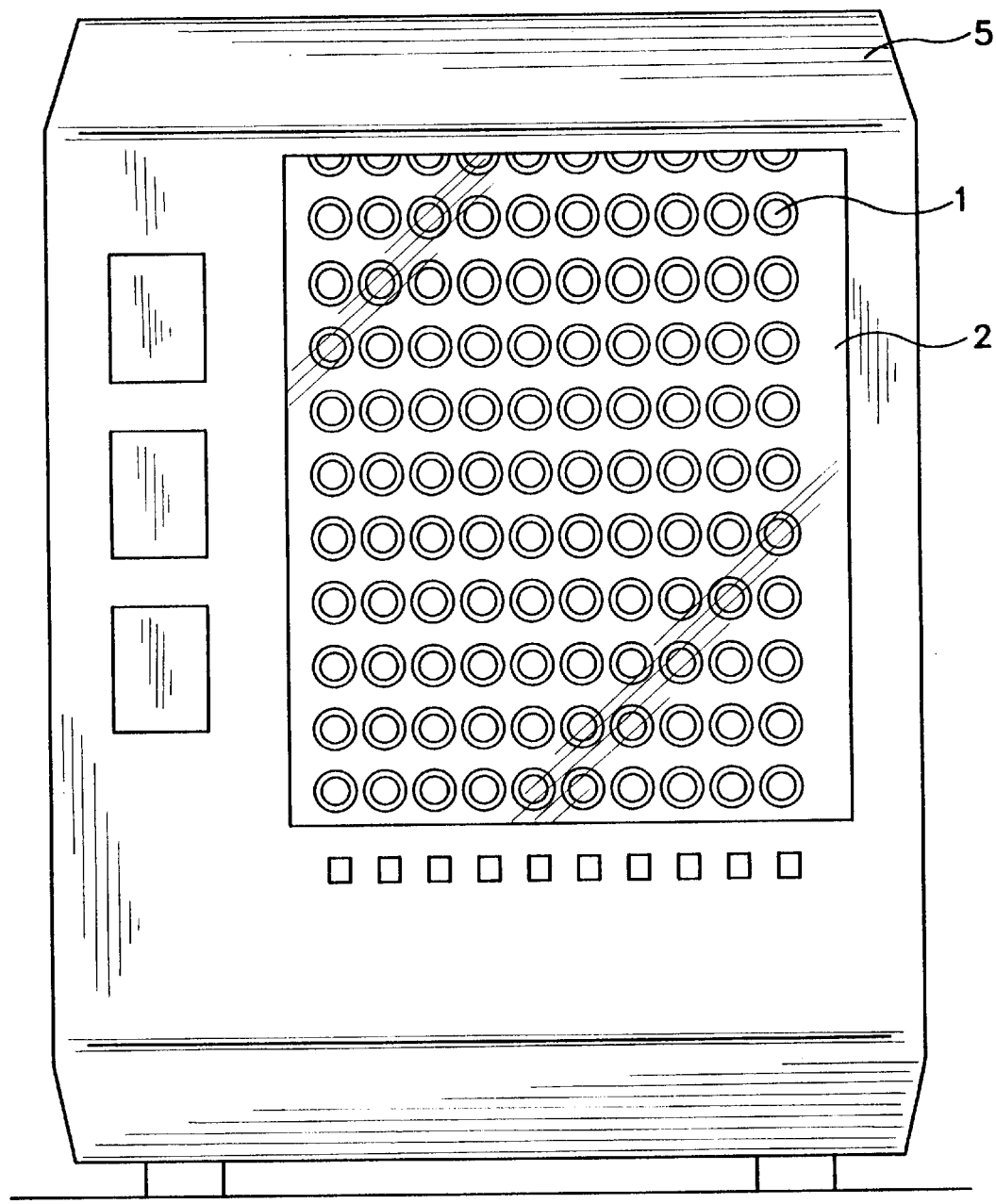
FIG. 4 shows a front-view of the blood culture apparatus according to the present invention with the front door open.

The depth of the whole instrument will be slightly larger than the drum diameter given in Table 1 due to the required thermally insulated housing. The width of the whole instrument will be somewhat larger than the drum's length due to the two ball-bearings and due to the insulated housing. It has been estimated that the footprint of an apparatus according to the present invention will be between 72% and 97% of the footprint of current systems. FIG. 3 shows a front-view of a blood culture apparatus according to the present invention, with door 13 closed. FIG. 4 shows a front-view of a 360-bottle blood culture apparatus according to the present invention with door 13 open.

Since the interior of bell-shaped drum 2 is utilized to accommodate control system 10 with its common photodetector and other major parts of the system's electronics, the space is thermally insulated from incubator 5 with access being provided from the second side 52 of instrument mainframe 50.

An apparatus according to the present invention has a very simple mechanical structure. The only moving part is hollow bell-shaped drum 2. Consequently, the production cost will be low, and the expected reliability is very high. Due to the fact that only one photodetector is used to read for all sensing stations 15, low sensitivity variations from one bottle station to the next can be expected, and a further reduction in the production cost is achieved. The apparatus also does not require electronic or optoelectronic components, electrical wires, or optical fibers on moving drum 2, which further increases the expected long-time reliability. Most important, the mechanical structure allows the user to grasp the bottles at their neck 23 during loading and unloading. Also, the apparatus offers simultaneous access to a large number of bottles 1 during loading and unloading.

Figure 5:
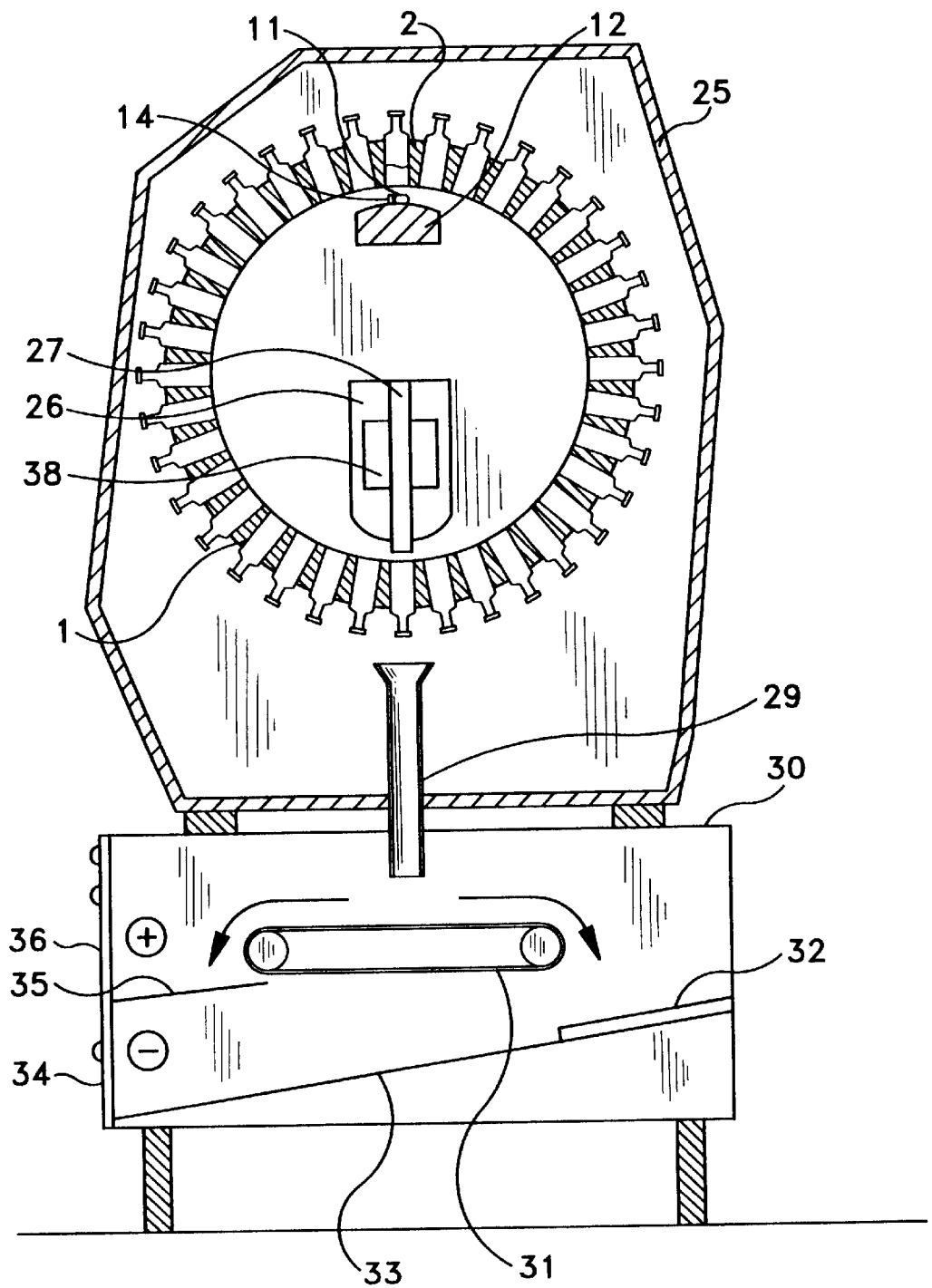
FIG. 5 shows a side-view of the interior of an alternative blood culture apparatus.
Figure 6:
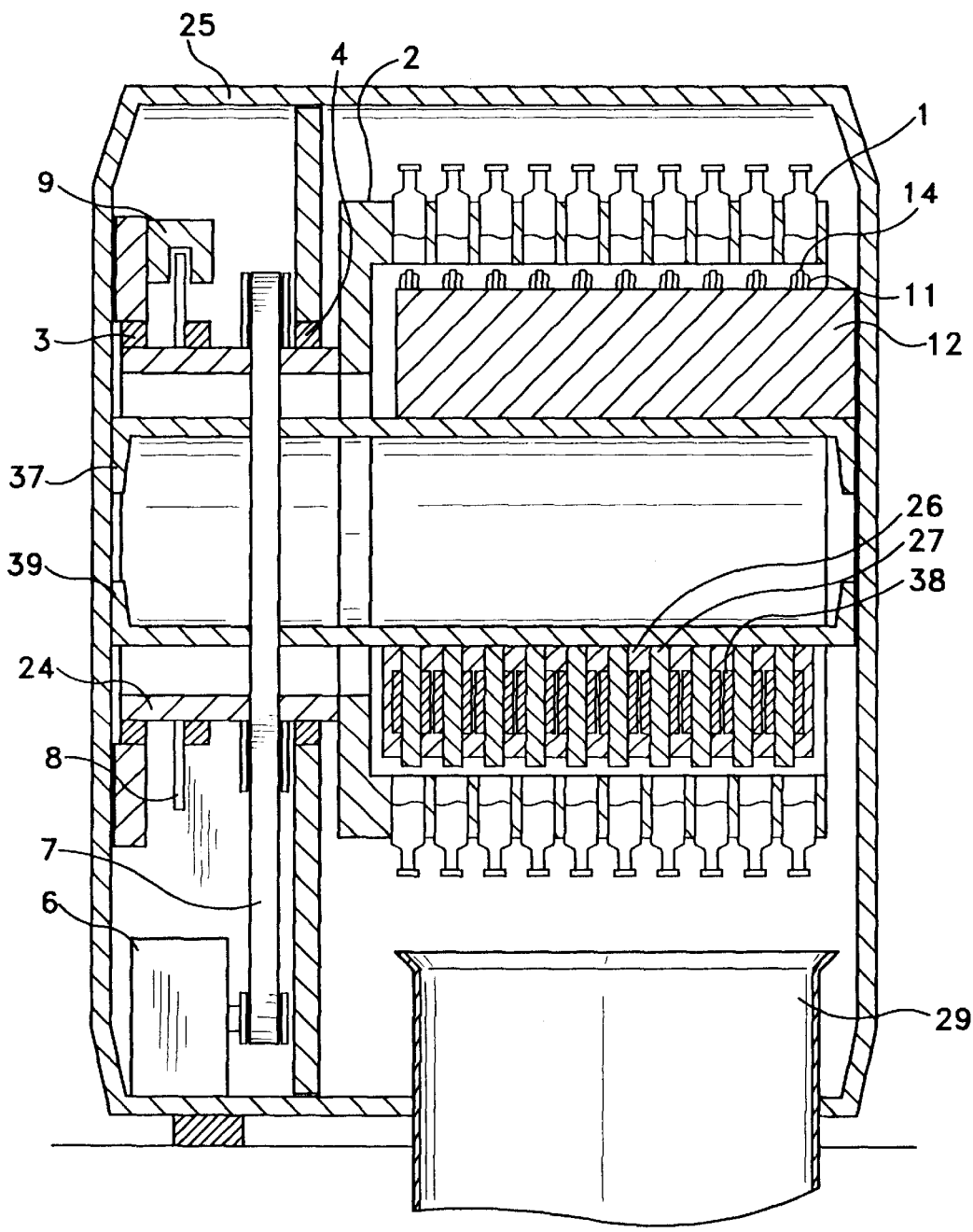
FIG. 6 shows a front view of the interior of the alternative blood culture apparatus shown in FIG. 5.

FIGS. 5 and 6 depict an improved alternative apparatus that offers the additional feature of self-unloading negative and positive blood culture bottles 1 into corresponding drawers 33 and 35. This feature reduces the workload for lab personnel, which is becoming an important issue in today's health care environment. Current blood culture systems do not provide such an "auto-unloading" feature.

As shown in the side view in FIG. 5, there is arranged a unit 26 within drum 2. Unit 26 comprises one piston 27 per drum segment that can be moved out of unit 26 by means of activators 38. If moved out of unit 26, piston 27 pushes one blood culture bottle 1 out of drum 2 located on the same radius of drum 2 as piston 27. In the apparatus of FIG. 5, there is arranged a collector 29 that receives bottle 1 and directs it onto a conveyer belt 31. If bottle 1 has been identified by system controller 10 as containing a final negative culture, conveyer belt 31 is activated by system controller 10 to move in a first direction. Then, as shown in FIG. 5, bottle 1 is transported to the right until it falls into "negative" drawer 33 in an area that is covered by a soft material 32 such as rubber foam and finally rolls towards "negative" door 34.

If bottle 1 has been identified by system controller 10 as containing a positive culture, conveyer belt 31 is activated by system controller 10 to move in a second direction. As shown in FIG. 5, bottle 1 is then transported to the left and falls into a "positive" drawer 35 to roll towards "positive" door 36.

For automatic unloading of final negative and positive blood culture bottles, drum 2 is stopped by control system 10 in a first appropriate orientation, and the corresponding final negative or positive bottle is ejected from drum 2. Then, control system 10 will rotate drum 2 to the next appropriate orientation, and the same procedure is repeated. This process is continued until all final negative bottles and all positive bottles are unloaded into the two drawers 33 and 35. Therefore, control system 10 can be programmed so that at the beginning of a workshift all final negatives are unloaded so that new bottles can be entered and all positive bottles are waiting in drawer 35 for further biological and/or chemical tests.

FIG. 6 is a front view of the apparatus that clearly shows brackets 37 and 39 inside bell-shaped drum 2 mounted to both ends of the instrument's mainframe 50. These two brackets 37 and 39 are used as stable platforms for linear sensor array 12 and unit 26 with its pistons 27 and activators 38. Of course, collector 29 can either be one single unit as shown in FIG. 6 or can be composed of individual collectors for each drum segment.

In the foregoing discussion, it is to be understood that the above-described embodiments of the present invention are simply illustrative of various features of a blood culture apparatus. Other suitable variations, modifications and combinations of these features could be made to or used in these embodiments and still remain within the scope of the present invention.

What is claimed is:

1. A blood culture apparatus comprising:

a housing;

a plurality of bottles having a bottom and a neck and containing a culture medium, specimen mixture, a headspace gas and optical sensing means;

a hollow drum rotatably mounted only to a first side of said housing and having an axis disposed therein, said drum being rotatable about said axis and including a plurality of openings for receiving said plurality of bottles;

a mechanism for rotating said drum about said axis; and detecting means in said drum for non-invasively detecting microorganisms within each of said plurality of bottles received within said drum wherein each bottle is oriented within one of said plurality of openings in said hollow drum towards said axis such that said optical sensing means in each bottle is visibly accessible to said detecting means from within said hollow drum through the bottom of each of bottle.

2. A blood culture apparatus according to claim 1, wherein each of said plurality of bottles is inserted into said drum base first so that said neck extends out of said opening.

3. A blood culture apparatus as recited in claim 1, further comprising positioning means for identifying the rotational position of said drum.

4. A blood culture apparatus as recited in claim 3, wherein said positioning means comprises an angular decoder mounted about said axis.

5. A blood culture apparatus as recited in claim 1, wherein said mechanism for rotating said drum comprises:

a shaft rotatably mounted only to said first side of said housing and secured to said drum; and a motor associated with said shaft to rotate said drum.

6. A blood culture apparatus as recited in claim 1, wherein said detecting means uses a non-invasive detection principle and comprises:

excitation light sources for emitting excitation light into each of said plurality of bottles in said drum; and light collectors for receiving light from each of said plurality of bottles.

7. A blood culture apparatus as recited in claim 6, wherein said optical sensing means is disposed on an inner bottom surface of each of said plurality of bottles; and said light collectors comprise collection fiber means for receiving light that reemerges from said optical sensing means.

8. A blood culture apparatus as recited in claim 1, wherein said hollow drum is bell-shaped.

* * * * *